US012628844B2

(12) United States Patent
Piispa et al.

(10) Patent No.: US 12,628,844 B2
(45) Date of Patent: May 19, 2026

(54) FAT SPREAD PRODUCT, PROCESS FOR PREPARING THE SAME, AND ITS USE AS TABLE SPREAD OR IN BAKERY

(71) Applicant: BUNGE NÖVÉNYOLAJIPARI ZÁRTKÖRUEN MUKÖDO RÉSZVÉNYTÁRSASÁG, Budapest (HU)

(72) Inventors: Eija Piispa, Paimio (FI); Laszlo Hornyak, Üllo (HU); Elzbieta Kozakiewicz, Mechelen (BE)

(73) Assignee: BUNGE NÖVÉNYOLAJIPARI ZÁRTKÖRUEN MUKÖDO RÉSZVÉNYTÁRSASÁG, Budapest (HU)

( * ) Notice: Subject to any disclaimer, the term of this patent is extended or adjusted under 35 U.S.C. 154(b) by 950 days.

(21) Appl. No.: 17/273,853

(22) PCT Filed: Sep. 13, 2019

(86) PCT No.: PCT/EP2019/074466
§ 371 (c)(1),
(2) Date: Mar. 5, 2021

(87) PCT Pub. No.: WO2020/053378
PCT Pub. Date: Mar. 19, 2020

(65) Prior Publication Data
US 2021/0307348 A1      Oct. 7, 2021

(30) Foreign Application Priority Data
Sep. 14, 2018      (EP) ..................................... 18194402

(51) Int. Cl.
*A23D 7/00*          (2006.01)
*A21D 2/16*          (2006.01)
(Continued)

(52) U.S. Cl.
CPC ............. *A23D 7/001* (2013.01); *A21D 2/165* (2013.01); *A23D 7/04* (2013.01); *C12P 7/6458* (2022.01)

(58) Field of Classification Search
CPC ......... A23D 7/001; A23D 7/04; C12P 7/6458; A21D 2/165
See application file for complete search history.

(56) References Cited

U.S. PATENT DOCUMENTS 6,231,914 B1 *    5/2001   Huizinga ................. A23D 9/00
                                                                426/607
2003/0161934 A1    8/2003   Floter
(Continued)

FOREIGN PATENT DOCUMENTS

EP         1 290 119 B1    10/2005
EP         2877034 B1 *    10/2018   ............. A23D 7/003
(Continued)

OTHER PUBLICATIONS

Sunflower Association: "Sunflower Oil Fatty Acid Profile;" 2010; Retrieved from the Internet: URL: https://www.sunflowernsa.com/uploads/35/sunflower-oil-fact-sheet_062510.pdf.
(Continued)

*Primary Examiner* — Erik Kashnikow
*Assistant Examiner* — Assaf Zilbering
(74) *Attorney, Agent, or Firm* — OLIFF PLC

(57)          ABSTRACT
A fat spread product including: at least 5% by weight of water; and from 10% to 95% by weight of a fat composition, wherein the fat composition included: from 10% to 100% by weight of an intraesterified fat or an interesterified fat blend, including HSHO sunflower oil or a fraction derived from HSHO sunflower oil; at most 85% by weight of at least one liquid oil or liquid oil mixture; and at most 5% by weight of at least one fat soluble additive.

8 Claims, 1 Drawing Sheet

Figure 1- Crystallization thermograms of different fat spreads

(51) Int. Cl.
    *A23D 7/04*         (2006.01)
    *C12P 7/6458*     (2022.01)

(56)         References Cited

U.S. PATENT DOCUMENTS

| | | | |
|---|---|---|---|
| 2006/0026714 A1* | 2/2006 | Martinez-Force | A61Q 1/06 |
| | | | 800/320.1 |
| 2015/0164101 A1* | 6/2015 | Pan | C11C 3/10 |
| | | | 426/601 |
| 2017/0049121 A1 | 2/2017 | Higgins et al. | |

FOREIGN PATENT DOCUMENTS

| | | | |
|---|---|---|---|
| WO | 95/20313 | A1 | 8/1995 |
| WO | 00/74470 | A1 | 12/2000 |
| WO | 2014/016245 | A1 | 1/2014 |
| WO | 2014/016250 | A1 | 1/2014 |
| WO | 2014/020114 | A1 | 2/2014 |

OTHER PUBLICATIONS

"Specifications for Margarine and Fat Spreads;" 2013; pp. 1-2; Retrieved from the Internet: URL: https://foodsafetyhelpline.com/2013/03/margarine-and-fat-spreads/.

Anushree et al.; "Stearic sunflower oil as a sustainable and healthy alternative to palm oil. A review;" Agronomy for Sustainable Development; 2017; pp. 1-10; vol. 37, No. 3.

Dec. 10, 2019 Search Report issued in International Patent Application No. PCT/EP2019/074466.

Mar. 9, 2021 International Preliminary Report on Patentability issued in International Patent Application No. PCT/EP2019/074466.

Salas, et al., "High stearic sunflower oil: Latest advances and applications." Oilseeds & fats Crops and Lipids. EDP Sciences, 2021. https://doi.org/10.1051/ocl/2021022.

"Standard for the fat spreads and blended spreads," Codex Stan 256-2007. p 1-5.

\* cited by examiner

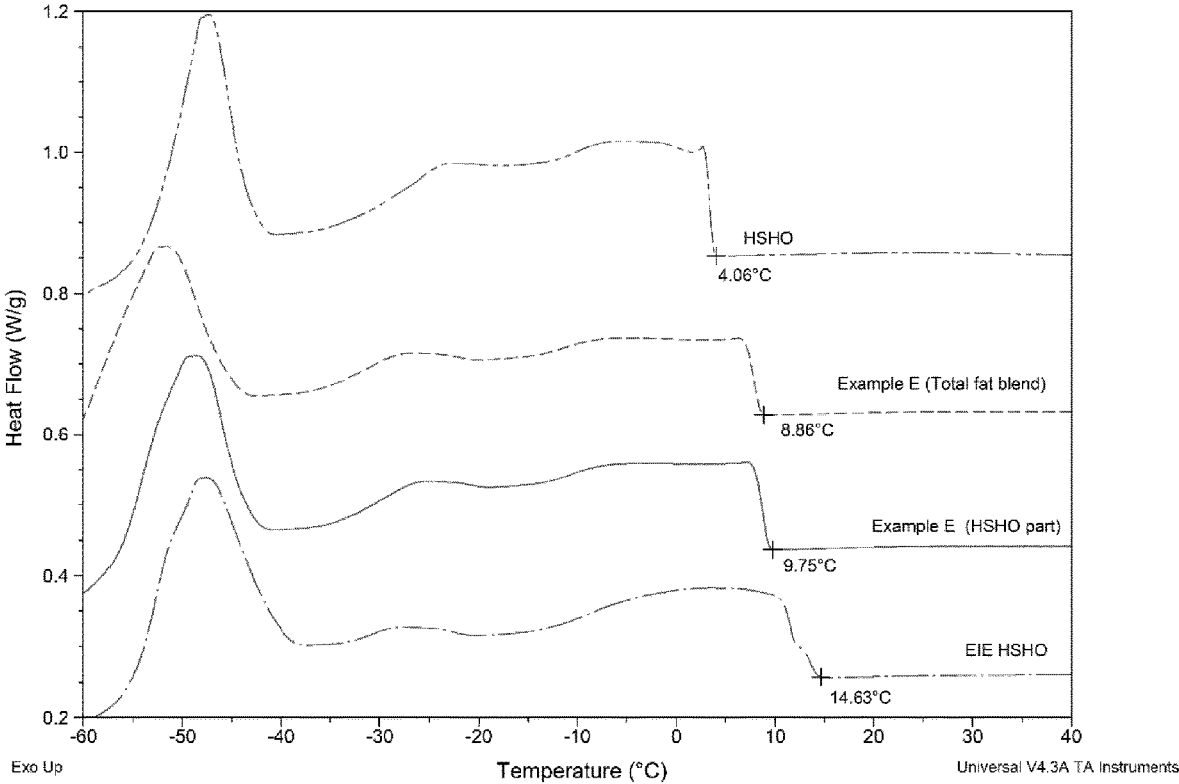
Exo Up
Universal V4.3A TA Instruments
*Figure 1- Crystallization thermograms of different fat spreads*

FAT SPREAD PRODUCT, PROCESS FOR PREPARING THE SAME, AND ITS USE AS TABLE SPREAD OR IN BAKERY

This invention relates to a fat spread product, uses thereof and a process to produce a fat composition suitable for preparing the fat spread product.

BACKGROUND

Fat spreads, such as margarine and table spread, have been available for more than 100 years. They consist in a water-in-oil (or water-in-fat) emulsion, with tiny droplets of water dispersed uniformly throughout a fat phase which is partially in a crystalline form or otherwise structured so that emulsion structure stays stable in storage conditions.

Emulsification is conducted at temperatures where fat blend and emulsifiers are in liquid forms. Water phase is added to liquid fat phase to achieve fat continuous emulsion. Final product obtained is a fat continuous spread. The obtained emulsion mixture is then crystallized and worked out to get the desired texture. Crystallization conditions mainly depend on the fat phase composition.

In some alternative processes, fat continuous spreads are produced using phase transfer process, where emulsion is first water continuous and is then transferred in process to fat continuous emulsion and final margarine.

The water phase generally comprises water, milk, milk proteins, sour milk or other milk preparation or milk proteins, or a mixture thereof to which are added further water-soluble ingredients such as salt, preservatives, water-soluble flavours or pH regulation agents.

The fat phase, also designated as fat blend, generally comprises liquid or semi-liquid oils or fats and a structure forming fat that is commonly named as 'hardstock', to which are added further fat soluble additives such as emulsifiers, vitamins and/or fat soluble flavours.

There is nevertheless a growing concern over the use of hydrogenated fats and palm fats in fat spreads. Numerous studies have linked the use of palm oil to heart and cardiovascular diseases, and suggest that excessive saturated fats and/or trans fats in the diet are a significant risk factor for cardiovascular events.

When developing new fat spreads compositions, it is also necessary to take care of its nutritional value. Most of fat spreads compositions on the market possess high nutritional value because of a high unsaturated fatty acids (such as oleic acid) content, but lack the relatively high stearic acid content.

The use of oils having a high content of oleic acid but also an increased stearic acid content in fat spread compositions has been reported. Commonly designated "HSHO" (high stearic high oleic) sunflower oils are an example of such oils. Such oils can be qualified of 'natural' because they are obtained by traditional breeding techniques. HSHO sunflower oils can be further fractionated to yield different kinds of stearin and olein fractions. The fractions can be used for various food applications, such as bakery, confectionery, frying or ice cream.

WO 00/74470 relates to plant seeds that contain an oil having an oleic acid content of more than 40 wt % and a stearic acid content of more than 12 wt % based on the total fatty acid content of said oil, and wherein a maximum of 10 wt % of the fatty acid groups in the sn-2 position of the TAG molecules constituting the oil are saturated fatty acid groups.

WO 95/20313 describes a sunflower seed, comprising a sunflower oil having an increased stearic acid content as compared to wild type seeds, obtainable by treating parent seeds with a mutagenic agent during a period of time and in a concentration sufficient to induce one or more mutations in the genetic trait involved in stearic acid biosynthesis resulting in an increased production of stearic acid, germinating the treated seeds and culturing progeny plants therefrom, collecting and analysing progeny seeds, selecting seeds that have acquired the desirable genetic trait and optionally repeating the cycle of germination, culturing and collection of seeds.

EP-A-1290119 concerns triglyceride fat comprising a stearin fraction of a high stearic, high oleic sunflower oil and a margarine fat phase comprising said stearin in admixture with a liquid vegetable oil in a weight ratio of 20:80 to 80:20.

EP-A-2880142 teaches a method for modifying one or more types of triglycerides in a fat or oil, comprising subjecting a single oil or fat selected from the group consisting of high stearic high oleic sunflower oil, high stearic high oleic soybean oil, high stearic high oleic rapeseed oil, and high stearic high oleic cottonseed oil, to an intraesterification process in which the fatty acids of the triglycerides of said oil or fat are randomly redistributed between the triglycerides to obtain an oil or fat with a modified solid fat content (SFC) profile, wherein the amounts of SUS type, SSU type and SSS type triglycerides and increased.

US 2003/0161934 describes a triglyceride fat which comprises HUU triglycerides and at least 18 wt. % of HOH and HLH triglycerides, while the ratio HOH:HLH is in the range 30/70 to 85/15, which fat is characterized in that the fat contains at least 20 wt. % of HUU and 8-30 wt. % of SOO triglycerides, where O denotes the residue of oleic acid, S of stearic acid, L of linoleic acid, U of oleic acid or linoleic acid and H denotes the residue of a saturated fatty acid with more than 15 carbon atoms with the proviso that at least 50 wt. % of the saturated fatty acids in HOH, HLH and HUU are stearic acid.

US 2017/0049121 relates to shortening compositions comprising a high stearic high oleic sunflower oil, a hard fat and optionally a cellulose fiber, wherein the hard fat is other than a palm fat.

DESCRIPTION OF THE INVENTION

There is a continuing need for healthier fat spreads having reduced saturated fatty acids levels (SAFA), while the fat spreads can still maintain acceptable structure, texture, appearance and organoleptic properties over several months of storage. There also remains a need for healthier fat spreads having improved crystallization behaviour in order to facilitate the processing and the handling of fat spreads, particularly being quick crystallizing and having a high temperature onset of crystallization.

According to the present invention, there is provided a fat spread product comprising:

at least 5% by weight of water;

and from 10% to 95% by weight of a fat composition, wherein the fat composition comprises:

from 10% to 100% by weight of an intraesterified fat or an interesterified fat blend comprising HSHO sunflower oil or a fraction derived from HSHO sunflower oil;

at most 85% by weight of one liquid oil or liquid oil mixture; and at most 5% by weight of at least one fat soluble additive. The fat spread of this invention has been found to be particularly healthy and surprisingly useful as table spread or for bakery applications. Fat spreads according to the invention provide not only particularly low palmitic acid and saturated acids level but also outstandingly favourable physical and organoleptic properties. In particular, the fat spread according to the invention provides good shelf life performance and crystallization properties.

In the context of the present invention:

the term "fat spread" refers to any product in the form of a solid, malleable emulsion, principally of the water-in-oil type, derived from solid and/or liquid vegetable and/or animal fats suitable for human consumption, with a milk-fat content which does not exceed 3% of the fat content. Preferably, "fat spread" designates margarine, three-quarter-fat margarine, half-fat margarine, table spread or fat spread X % as defined in Appendix to Annex XV of EC Regulation 1234/2007;

the term "fat" refers to glyceride fats and oils containing fatty acid acyl groups and does not imply any particular melting point. The term "oil" is used synonymously with "fat";

the term "intraesterified fat" refers to a fat in which fatty acids positions in triglyceride molecules are changed by a chemical or enzymatic process to modify triacylglycerols chemical, physical and/or nutritional properties. Intraesterification is conducted on a single fat;

the term "interesterified fat blend" refers to a fat blend in which fatty acids positions in triglyceride molecules are changed by a chemical or enzymatic process to modify triacylglycerols chemical, physical and/or nutritional properties. Interesterification is conducted on a mixture of different fats or different fractions of fats;

the term "liquid oil" refers to any single edible oil being in a liquid state at room temperature;

the term "fat soluble additive" refers to minor fat soluble components that are added to fat blend and have functional, taste or nutritional effect in final fat spread. Examples of fat soluble additive includes emulsifiers, vitamins and fat soluble flavours;

the term "fatty acid", as used herein, refers to straight chain saturated or unsaturated (including mono- and polyunsaturated) carboxylic acids having from 8 to 24 carbon atoms. A fatty acid having n carbon atoms and x double bonds may be denoted Cx:y. For example, palmitic acid may be denoted C16:0 and oleic acid may be denoted C18:1. Percentages of fatty acids in compositions referred to herein include acyl groups in tri-, di- and mono-glycerides present in the glycerides and are based on the total weight of C8 to C24 fatty acids. The fatty acid profile (i.e., composition) may be determined, for example, by fatty acid methyl ester analysis (FAME) using gas chromatography according to ISO 12966-2 and ISO 12966-4; the term "saturated fatty acid" (SAFA) and "saturated fat" both refer to a saturated acid containing from to 8 to 24 carbon atoms and having no double bonds between the individual carbon atoms of the fatty acid chain (i.e. the chain of carbon atoms is fully "saturated" with hydrogen atoms);

the term "fraction derived from HSHO sunflower oil" refers to an oil or fat obtained from HSHO sunflower oil by one or more steps of dry or wet fractionation, which are well known techniques in the art.

the term "TAG" designates triacylglycerol molecules, with a glycerol backbone and 3 fatty acids esterified to it. TAGS are named by three letters representing the fatty acids that are esterified on it at the different 3 positions of the glycerol molecule, said fatty acids being saturated ("S") or unsaturated ("U");

"S" designates saturated fatty acids such as palmitic, stearic, arachidic and behenic acids;

"U" designates unsaturated fatty acids such as oleic, linoleic and linolenic acids;

"SSS" designates trisaturated TAG, calculated from detailed TAG species results;

"UUU" designates triunsaturated TAG, calculated from detailed TAG species results;

"SUU" designates diunsaturated TAG, calculated from detailed TAG species results;

"SUS" designates disaturated TAG, calculated from detailed TAG species results;

amounts of triglycerides specified herein are percentages by weight based on total triglycerides present in the fat composition. The notation triglyceride XYZ denotes triglycerides having fatty acid acyl groups X, Y and Z at any of the 1-, 2- and 3-positions of the glyceride. The notation A2B includes both AAB and ABA, and AB2 includes both ABB and BAB. Triglyceride content may be determined for example by GC. When referring to triglyceride, "P", "St", "O", "L", "Ln", "A" and "B" respectively refer to palmitic, stearic, oleic, linoleic, linolenic, arachidic and behenic acids, respectively. Each GC peak includes triglycerides having the same fatty acids in different positions e.g., POSt is in the same signal peak as PStO;

"SFC" designates Solid Fat Content measured by NMR (nuclear magnetic resonance) as the percentage mass fraction of fat in the solid state according to the ISO 8292-1:2008 method for non-stabilised fats;

the term "at most 'X' %" refers to a range of from 0% to 'X' %; and unless otherwise specified, all % values are weight %.

The present invention relates to a fat spread product comprising at least 5% by weight of water; and from 10% to 95% by weight of a fat composition, wherein the fat composition comprises from 10% to 100% by weight of an intraesterified fat or an interesterified fat blend, comprising HSHO sunflower oil or a fraction derived from HSHO sunflower oil; at most 85% by weight of one liquid oil or liquid oil mixture; and at most 5% by weight of at least one fat soluble additive.

Preferably, the present invention relates to a fat spread product as defined above possessing the following characteristics, taken individually or in combination:

the fat spread product contains from 15% to 95% by weight of a fat composition, more preferably from 25% to 90% by weight of a fat composition, even more preferably from 35% to 85% by weight of a fat composition;

the fat spread product contains from 5% to 90% by weight of water, more preferably from 10% to 80% by weight of water, even more preferably from 20% to 70% by weight of water;

the fat composition comprises from 20% to 100% by weight of an intraesterified fat or an interesterified fat blend, comprising HSHO sunflower oil or a fraction derived from HSHO sunflower oil;

the fat composition comprises from 10% to 100% by weight of intraesterified HSHO sunflower oil, more preferably from 20% to 100% by weight of intraesterified HSHO sunflower oil;

HSHO sunflower oil of the fat composition used in the fat spread product contains from 14% to 27% by weight of stearic acid (C18:0), more preferably from 16% to 25% by weight of stearic acid (C18:0);

HSHO sunflower oil of the fat composition used in the fat spread product contains from 20% to 35% by weight of saturated fatty acids (SAFA), more preferably from 22% to 33% by weight of saturated fatty acids (SAFA);

the fat composition comprises at most 80% of at least one liquid oil;

the fat composition has a solid fat content at 10° C. of from 2% to 10% and a solid fat content at 20° C. of from 1% to 4%; more preferably the fat composition has a solid fat content at 10° C. of from 4% to 6% and a solid fat content at 20° C. of from 2% to 3%.

the fat composition comprises at least 0.2% by weight based on total triglycerides present in the fat composition of StStSt and at most 32% by weight based on total triglycerides present in the fat composition of StOO, more preferably at least 0.4% by weight based on total triglycerides present in the fat composition of StStSt and at most 30% by weight based on total triglycerides present in the fat composition of StOO;

the liquid oil is selected from rapeseed oil, canola oil, sunflower oil, high oleic sunflower oil, HSHO sunflower oil, soybean oil, olive oil, corn oil, safflower oil, sesame oil, peanut oil and camelina oil;

the fat composition contains at most 2.5%, preferably at most 1% of fat soluble additive; and/or the fat soluble additive is selected from emulsifiers, vitamins, preservatives, antioxidants and fat soluble flavours.

In addition to the fat composition and the water, the fat spread according to the present invention may further contain some typical ingredients such as dairy components among which milk, cream, yogurt and quark; emulsifiers among which mono- and diglycerides (E471), lecithins, polyglycerol polyricinoleate (E476), esters of mono- and diglycerides (E472a-f), propyleneglycol esters of fatty acids (E477) and polyglycerol esters of fatty acids (E475); annatto or beta carotene; vitamin A; vitamin D; vitamin E; salt; citric acid; preservatives among which sorbic acid or its salts and EDTA; thickeners among which gelatine, starches and pectines; flavor agents; antioxidants such as tocopherols.

The invention also relates to the use of a fat spread product according to the invention as table spread or for a bakery application. In a preferred embodiment, the bakery application is pastries, cakes, doughnuts or cookies.

Fat spreads of the invention may, for example, be used as table spread as such. The table spread may consist of oils and fats, milk, water, emulsifier, vitamins and other ingredients.

Fat spreads of the invention may also, for example, be used in the production of bakery products. The bakery products may have a laminated structure. Fat spreads of the invention may be combined with flour and water to form a dough. The dough preferably comprises flour in an amount of from 30 to 60% by weigh, water in an amount of from 10 to 40% by weight, fat spread or laminating fat in an amount of from 20 to 40% by weight and from 0.04% to 0.75% by weight of emulsifier based on the weight of the dough. Optionally, one or more further ingredients such as salt and flour modifier may be included in the dough. Bakery products may be made from dough. The dough preferably has a laminated structure. The bakery products include, for example, puff pastry, croissants, Danish pastries and pies.

Doughs comprising the fat spread may be refrigerated, frozen or otherwise stored prior to use. The frozen dough may be packaged and sold to the consumer. In order to form a bakery product, the dough is baked, preferably in an oven.

Cake may be made from a batter that is baked. Cake batters typically comprise fat spread, emulsifier, sugar, flour, milk and eggs. The amount of fat spread in the batter is typically in the range of 3% to 40% by weight.

Doughnuts are usually deep-fried from a flour dough. Doughnuts typically comprise fat spread, flour, water, leavening, eggs, milk, sugar, oil and flavours. Further, various toppings and flavourings may be used, such as sugar, chocolate or glazing. The amount of fat spread in the batter is typically in the range of 5% to 30% by weight. Cookie may also be made from a dough that is baked. Cookie batters typically comprise fat spread, sugar, milk, flour, salt, flour or optionally confectionery product such as chocolate. The amount of fat spread in the batter is typically in the range of 5% to 30% by weight.

The invention also relates to a process for making the fat composition contained in the fat spread product according to the present invention. Accordingly, the present invention also relates to a process for preparing the fat composition contained in the fat spread product according to the present invention, said process comprising the blending of an intraesterified fat or an interesterified fat blend comprising HSHO sunflower oil or a fraction derived from HSHO sunflower oil; one liquid oil or liquid oil mixture; and at least one fat soluble additive.

Preferably, the blending is proceeded by the steps of:

providing a fat or fat blend comprising HSHO sunflower oil or a fraction derived from HSHO sunflower oil; and enzymatic interesterification of the fat or fat blend to produce the intraesterified fat or interesterified fat blend.

The process of the invention may also comprise the step of bleaching and/or deodorization, typically after intraesterification or interesterification, before or after blending and any optional fractionation.

The fat spread according to the present invention can be prepared according to classical processes known by the skilled artisan. As an example, fat spread according to the present invention can be prepared by a process comprising the following steps:

preparation of a concentrated water soluble ingredients such as salt, acids, thickeners, dairy solids, preservatives and flavour agents which are dissolved in water phase in the desired proportion in weighing tanks;

emulsification of the thus obtained water phase and a fat blend according to the present invention in a stirring tank in a ratio of 10/90 to 85/15 (fat content 15-90%, water 85-10%) by adding water phase to fat phase; or, alternatively, the fat blend according to the present invention and the water phase are mixed together by using a proportioning pump;

heating the obtained emulsion to ensure a perfect microbiological safety to the finished product;

cooling said emulsion in dedicated equipment to allow crystallization while submitting to high shear to allow development of tiny fat crystals necessary.

Preferences and options for a given aspect, embodiment, feature or parameter of the invention should, unless the context indicates otherwise, be regarded as having been disclosed in combination with any and all preferences and options for all other aspects, embodiments, features and parameters of the invention.

The following non-limiting examples illustrate the invention and do not limit its scope in any way. In the examples and throughout this specification, all percentages, parts and ratios are by weight unless indicated otherwise.

EXAMPLES

Example 1—High Stearic Sunflower Oil and Enzymatic Intraesterified High Stearic Sunflower Oil High Stearic Sunflower Oil (HSHO) can be obtained from high stearic sunflower seeds using standard oil pressing, refining and deodorization process. Deodorized HSHO oil can be used as ingredients as such for fat spreads and as raw material for preparing of intraesterified EIE HSHO (by enzymatic intraesterification) which can be also used as ingredient for fat spreads.

Enzymatic intraesterification of high stearic sunflower oil (EIE HSHO) was conducted following the protocol reported in Table 1 below.

TABLE 1

| Protocol (EIE): | Added material | Temp. (° C.) | Dosage | Reaction time, under mixing | Pressure | Controlled parameters |
|---|---|---|---|---|---|---|
| Heating/ drying of fat blend | — | 80° C. | — | | 10 mbar | Water content (<50 mg/kg) |
| Enzyme (Lipozyme TL IM) preparation- drying | — | 70° C. | 5.00% | 30 min | 20 mbar | Temp |
| Intraesterification- enzymatic | — | 70° C. | — | 8 hours | 100 mbar | Temp |
| Deodorization | N$_2$/H$_2$O | 235° C. | 5 ml/h/kg | 2 hours | 2 mbar | Free fatty acids |

As an alternative starting material for interesterification, fractions of HSHO sunflower oil and mixtures thereof can also be used to obtain comparable properties. In particular, stearins from HSHO sunflower oil are useful. Examples of suitable methods for wet and dry fractionation of HSHO sunflower oil are given in Bootello M A et al., Food Chem. 2015 Apr. 1; 172:710-7.

Example 2—Process for Preparing a Fat Spread Composition

First, a fat phase made of all fat soluble ingredients and a water phase made of all water soluble ingredients including are prepared.

Fat phase and water phase are heated up to 70° C. and emulsion is formed by adding water phase to fat phase under constant stirring.

Emulsion is crystallized in standard pilot scale margarine process using a Gerstenberg & Agger pilot perfector.

Finally, the products were packed in plastic tubs and stored at both 5° C. and 10° C.

Example 3—Fat Spread Compositions A to J

Fat spreads A to J have been prepared according to the process of Example 2.

Compositions of obtained fat spreads are reported in Tables 2 and Table 3 below.

Fat spreads A to E illustrate the invention under discussion whereas fat spreads F to J are cited as comparative examples.

TABLE 2

| | Fat spreads A to E | | | | |
|---|---|---|---|---|---|
| | Fat spreads | | | | |
| Ingredient | A | B | C | D | E |
| Enzymatically intraesterified high stearic sunflower oil (EIE HSHO) | 59.34 | 53.33 | 39.38 | 13.50 | 27.00 |
| High Stearic Sunflower Oil (HSHO) | — | — | — | 39.82 | 26.33 |
| Rapeseed oil | — | 6.00 | — | 6.00 | 6.00 |
| Emulsified Dimodan P PEL/B | 0.40 | 0.40 | 0.50 | 0.40 | 0.40 |
| Emulsifier PGPR | — | — | 0.10 | — | — |
| Sunflower lecithine | 0.25 | 0.25 | | 0.25 | 0.25 |
| Beta-carotene 30% solution | 0.0025 | 0.0025 | 0.0025 | 0.0025 | 0.0025 |
| Fat soluble butter flavour | 0.020 | 0.025 | 0.020 | 0.025 | 0.025 |
| Water | 39.49 | 39.19 | 59.49 | 39.19 | 39.19 |
| Salt | 0.50 | 0.80 | 0.50 | 0.80 | 0.80 |
| Water soluble butter flavour | 0.0034 | 0.0034 | 0.0034 | 0.0034 | 0.0034 |
| Total | 100.0 | 100.0 | 100.0 | 100.0 | 100.0 |
| Total fat content in the fat spread | 60.0 | 60.0 | 40.0 | 60.0 | 60.0 |
| % of intraesterified HSHO in the fat blend (*) | 98.9% | 88.8% | 98.4% | 22.5% | 45.0% |

(*): fat blend includes all fat soluble components

TABLE 3

| | Comparative fat spreads F to J | | | | |
| | Fat spreads | | | | |
| Ingredient | F | G | H | I | J |
|---|---|---|---|---|---|
| Enzymatically intraesterified high stearic sunflower oil (EIE HSHO) | — | — | — | — | 5.40 |
| High Stearic Sunflower Oil (HSHO) | 39.38 | 35.47 | 59.32 | 79.34 | 47.93 |
| Rapeseed oil | — | 4.01 | — | — | 6.00 |
| Emulsified Dimodan P PEL/B | 0.50 | 0.50 | 0.40 | 0.40 | 0.40 |
| Emulsifier PGPR | 0.10 | 0.10 | | | — |
| Sunflower lecithine | — | — | 0.25 | 0.25 | 0.25 |
| Beta-carotene 30% solution | 0.0025 | 0.0025 | 0.0025 | 0.0025 | 0.0025 |
| Fat soluble butter flavour | 0.020 | 0.025 | 0.020 | 0.020 | 0.025 |
| Water | 59.49 | 59.09 | 39.48 | 19.48 | 39.19 |
| Salt | 0.50 | 0.80 | 0.50 | 0.50 | 0.80 |
| Water soluble butter flavour | 0.0034 | 0.0034 | 0.0340 | 0.0034 | 0.0034 |
| Total | 100.0 | 100.0 | 100.0 | 100.0 | 100.0 |
| Total fat content in the fat spread | 40.0 | 40.1 | 60.0 | 80.0 | 60.0 |
| % of intraesterified HSHO in the fat blend (*) | 0% | 0% | 0% | 0% | 9.0% |

(*): fat blend includes all fat soluble components

Example 4—Fatty Acids Composition of Fat Composition without Emulsifier in Fat Spread A to J Fatty acids composition (in % of total fat) of fat composition without emulsifier in fat spreads A to J is reported in the Table 4 below. Cx:y refers to a fatty acid having x carbon atoms and y double bonds; levels determined by GC-FAME (ISO 12966-2 and ISO 12966-4).

TABLE 4

| | Fatty acid composition of fat spread compositions A to J | | |
| Fatty acid | Fat spreads A, C & comparative fat spreads F, H, I | Fat spreads B, D, E & comparative fat spreads G, J | Rapeseed oil |
|---|---|---|---|
| C16:0 | 5.2 | 5.0 | 4.8 |
| C16:1 | 0.1 | 0.1 | 0.1 |
| C18:0 | 17.2 (*) | 15.6 (**) | 2.0 |
| C18:1 | 69.7 | 69.0 | 64.1 |
| C18:2 w6 | 3.8 | 5.6 | 18.6 |
| C18:3 w3 | 0.1 | 1.1 | 8.2 |
| C20:0 | 1.3 | 1.2 | 0.7 |
| C20:1 | — | 0.1 | 1.2 |
| C22:0 | 1.9 | 1.7 | 0.3 |
| C24:0 | 0.3 | 0.3 | 0.0 |
| Saturated fatty acids | 25.9* | 23.8 (***) | 7.8 |
| Other fatty acids | 0.4 | 0.3 | 0.0 |

(*) No liquid oil in recipe. all C18:0 and saturated fatty acids are from HSHO sunflower oil source
(**) 1.3% of stearic acid comes from rapeseed oil (liquid oil) and 98.7% of stearic acid comes from HSHO sunflower oil source
(***) 2.5% of saturated fatty acids come from rapeseed oil (liquid oil) and 97.5% of saturated fatty acids come from HSHO sunflower oil source

Example 5: Solid Fat Content of the Fat Composition in Fat Spreads A, C, F, H and I Solid fat content (%) of the fat compositions in fat spreads A and C, comparative fat spreads F, H and I, classical butter and tub margarine is reported in the Table 5 below. Solid fat content (%) is determined by NMR on unstabilised fat at 10, 20, 30, 35 and 40° C. (ISO 8292-1).

TABLE 5

| | Solid fat contents | | | | |
| | SFC (%) | | | | |
| Sample | 10° C. | 20° C. | 30° C. | 35° C. | 40° C. |
|---|---|---|---|---|---|
| Comparative fat spreads F, H, I | 1.6 | 0.2 | 0.4 | 0.3 | 0.3 |
| Fat spreads: A, C | 4.5 | 2.7 | 1.6 | 0.8 | 0.6 |
| Butter | 45 | 20 | 7 | 1 | 0 |
| Tub margarine fat blend (standard with 35% palm based hardstock and 65% liquid oil) | 21 | 12 | 5 | 3 | 2 |

As evidenced by Table 5, fat spreads of the invention contain very low levels of solid fat at standard measurement temperatures 10° C. to 40° C. compared to standard butter and tub margarine fat spread.

Solid fat content measurement is standard analytics when evaluating fat blends suitability for spreads. SFC results <5% at 10° C. and <3% at 20° C. confirm existence of a significant difference between fat spreads A and C according to the invention and 'Tub margarine bat blend'. A skilled artisan would not have considered fat spreads A and C according to the invention as suitable for preparing fat spreads without addition of hardstock in order to obtain the desired structure.

However, it is also believed that the structure and the texture of fat spreads could not be maintained properly when they have solid fat content lower than 2% at 10° C. and lower than 1% at 20° C., such as comparative fat spreads F, H and I.

Example 6: Triglyceride Composition of Fat Composition in Fat Spreads

The composition of TAG species was analyzed by gas chromatography of an Agilent 7890 gas chromatograph endowed with a 30 m. Quadrex aluminium-clad bonded methyl 65% phenyl silicone capillary column, 0.25 mm ID., 0.1 micron film thickness, using hydrogen as the carrier gas and FID detector according to Fernandez-Moya et al. J. Agr. Food Chem. 2000, 48:764-769. TAG classes (SSS, SUS, SUU, UUU) were calculated from detailed TAG species results. Each GC peak includes triglycerides having the same fatty acids in different positions e.g., POSt is in the same signal peak as PStO.

TABLE 6

| Triglyceride (%) | Samples F, H, I (Comparative fat spreads F, H, I without fat soluble additives) | Samples A, C (Fat spreads A, C without fat soluble additives) | Sample E (Fat spread E without fat soluble additives) |
|---|---|---|---|
| PStP | 0.0 | 0.2 | 0.1 |
| POP | 0.9 | 0.8 | 0.8 |
| PLP | 0.1 | 0.1 | 0.1 |
| PStSt | 0.0 | 0.6 | 0.3 |
| POSt | 4.6 | 4.5 | 4.2 |
| POO | 10.4 | 9.0 | 9.5 |
| PLSt | 0.3 | 0.3 | 0.3 |
| POL | 0.8 | 0.9 | 1.2 |
| POLn | 0.0 | 0.0 | 0.1 |
| PLL | 0.4 | 0.2 | 0.4 |
| StStSt | 0.0 | 0.7 | 0.4 |
| StOSt | 6.1 | 6.7 | 5.9 |
| StOO | 34.2 | 26.1 | 28.0 |
| StLSt | 0.4 | 0.9 | 0.7 |
| OOO | 29.9 | 35.0 | 32.1 |
| StOL | 2.1 | 3.3 | 3.2 |
| OOL | 2.5 | 5.0 | 4.8 |
| StLL | 0.1 | 0.4 | 0.6 |
| StLLn + StLnLn | 0.0 | 0.0 | 0.6 |
| OLL | 0.8 | 0.6 | 1.4 |
| StOA | 1.1 | 1.2 | 1.0 |
| OOA | 2.3 | 1.6 | 1.7 |
| OLA | 0.1 | 0.0 | 0.1 |
| LLL | 0.0 | 0.0 | 0.1 |
| StOB | 0.6 | 0.7 | 0.6 |
| OOB | 2.3 | 1.1 | 1.5 |
| SSS | 0.0 | 1.5 | 0.8 |
| SUS | 14.0 | 15.4 | 13.8 |
| SUU | 52.7 | 42.6 | 47.1 |
| UUU | 33.3 | 40.6 | 38.2 |

Example 7: Crystallization Thermogram

FIG. 1 shows the crystallization thermogram as obtained by differential scanning calorimetry (DSC) after applying the following program:
1) Heating up to 90° C. at a rate of 20° C./min.
2) Isothermal at 90° C. for 5 minutes.
3) Cool down from 90° C. to −80° C. at a rate of 10° C./min.

As shown in this FIGURE, Sample E—'HSHO part' (Blend of EIE HSHO and HSHO without rapeseed oil and fat soluble additives) and Sample E—'Total fat blend' (blend of EIE HSHO, HSHO and rapeseed oil but without fat soluble additives) begin to crystallize at higher temperatures than non-intraesterified fat (HSHO).

Sample E crystallization curves exhibit intermediate onsets of crystallization compared to HSHO (4.06° C.) and EIE HSHO (14.63° C.). The addition of liquid oil in "Sample E—Total fat blend" slightly reduces the onset of crystallization (8.86° C.), but it is still higher than HSHO oil.

Therefore, the fat spread E according to the invention has improved crystallization behaviour with a high temperature onset. This crystallization behaviour indicates a good processability and stable behaviour.

12

Example 8: Sensory Evaluation of Fat Spread a to J

Spreadability, emulsion stability and melting behaviour of fat spreads A to E and comparative fat spreads F to J were evaluated by sensory evaluation and compared to commercial fat spreads with same fat content, i.e. 40%, 60% and 80% fat respectively.

Sensory experts trained to evaluate such characteristics of fat spreads were asked to make this comparison using agreed scoring of good product.

Fresh samples fat spreads A to E and comparative fat spreads F to J have scoring in sensory evaluation that is comparable to products available on the market. Both fat spreads A to E and comparative fat spreads F to J have in particular smooth spreadability and no emulsion breakage is observed. Fat spreads A to E and comparative fat spreads F to J have also melting behaviour comparable to commercial samples with same total fat content.

During shelf life (being 4 to 6 months), it appeared that sensory evaluation results became unacceptable and unsatisfactory for comparative fat spreads F to J. These fat spreads lost the proper texture and became 'sandy'. Their structure was not acceptable anymore at the end of shelf life. However, fat spreads A to E according to the invention showed still the good structure, texture, appearance and organoleptic properties.

These results combined with the results reported in Table 4 evidence that, despite fatty acid composition is the same, fat spreads A to E according to the invention are particularly stable in long term shelf life test comparing to comparative fat spreads F to J.

Finally, the taste of fat spreads A to E (fresh and at the end of shelf life) was evaluated and considered as comparable to commercial products with the same flavour affecting ingredients, in particular salt content and flavours.

Example 9: Fatty Acid Composition of Fat Spreads a to E and Comparative Fat Spreads F to J and Effect on Cholesterol Level The effect on cholesterol level of fat spread compositions A to E and comparative fat spreads F to J has been calculated in light of the fatty acid compositions reported in Table 4. As cholesterol level effect results from fatty acid composition, it does not make difference between processing method of oils, thus HSHO and EIE HSHO oil results in same effect on cholesterol levels.

Method of Calculation

Effect of high stearic sunflower oil as well as some comparison fats/fat blends on the cholesterol level has been calculated using the factors reported by European Food Safety Administration (EFSA) (Estimated effects for the change in serum lipids and lipoproteins for a group of subjects when one percent of energy in the diet from carbohydrates is replaced isocalorically by a particular fatty acid) of the Opinion of the Scientific Panel on Dietetic Products, Nutrition and Allergies on a request from the Commission related to the presence of trans fatty acids in foods and the effect on human health of the consumption of trans fatty acids, EFSA Journal (2004), 81, 1-49.

According to this method, the cholesterol lowering effect of a fat blend can be calculated using the following formula:

Total cholesterol (TC) mmol/L change=+0,031*trans-monounsaturated fatty acids+

0.069*lauric acid+0.059*myristic acid+0.041*palm-
itic acid−0.01*stearic acid−

0.006*cis-monounsaturated fatty acids−0.021*cis
polyunsaturated fatty acids,

LDL mmol/L change=+0.040*trans-monounsaturated
fatty acids+0.052*lauric acid+

0.048*myristic acid+0.039*palmitic acid−
0.004*stearic acid−0.009*cis-monounsaturated fatty acids−0.019*cis polyunsaturated fatty acids.

Results

Cholesterol lowering effect has been calculated based on a 100% fat which represents cholesterol lowering effect of fat or bat blend. This effect can be calculated also for fat blends of existing products, like butter fat, giving opportunity to compare different fats/fat blends effect on cholesterol levels.

The obtained calculated results are reported in the Table 7 below.

TABLE 7

| Cholesterol effect of fat spreads fat blend | | | |
|---|---|---|---|
| Sample | Saturated fat % of total fatty acid composition | TC change (mmol/L) | LDL change (mmol/L) |
| Fat blend of fat spreads A, C, F, H, >I | 25.9 | −0.46 | −0.56 |
| Fat blend of fat spreads B, D, E, G, J | 23.8 | −0.50 | −0.61 |
| Butter fat | 68.8 | 1.82 | 1.61 |
| Fat blend from Vita Hjertego 70%, commercial margarine with low saturated fat content | 22.4 | −0.36 | −0.44 |
| Rapeseed oil | 8.10 | −0.79 | −0.91 |

The calculated cholesterol lowering effect of fats spreads according to the present invention is more important than the cholesterol lowering effect of commercial margarine (Vita Hjertego 70%) containing less saturated fat. This indicates that spreads according to the present invention possess a better health effect.

The invention claimed is:

1. A fat spread product comprising:
at least 5% by weight of water; and
from 10% to 95% by weight of a fat composition, wherein the fat composition comprises:
from 20% to 100% by weight of an unfractioned intraesterified HSHO sunflower oil;
at most 80% by weight of at least one liquid oil; and
at most 3% by weight of at least one fat soluble additive,
wherein the fat composition comprises:
at least 0.2% by weight, based on total triglycerides present in the fat composition, of StStSt; and
at most 32% by weight, based on total triglycerides present in the fat composition, of StOO.

2. The fat spread product according to claim 1, comprising from 15% to 95% by weight of the fat composition.

3. The fat spread product according to claim 1, comprising from 5% to 90% by weight of water.

4. The fat spread product according to claim 1, wherein the HSHO sunflower oil in the fat composition contains from 14% to 27% by weight of stearic acid (C18:0).

5. The fat spread product according to claim 1, wherein the HSHO sunflower oil in the fat composition contains from 20% to 35% by weight of saturated fatty acids.

6. The fat spread product according to claim 1, wherein the at least one liquid oil is selected from the group consisting of rapeseed oil, canola oil, sunflower oil, high oleic sunflower oil, HSHO sunflower oil, soybean oil, olive oil, corn oil, safflower oil, sesame oil, peanut oil and camelina oil.

7. The fat spread product according to claim 1, wherein the fat soluble additive is selected from the group consisting of emulsifiers, vitamins, preservatives, antioxidants and fat soluble flavours.

8. The fat spread product according to claim 1, wherein the fat composition has:
a solid fat content at 10° C. of from 2% to 10%; and
a solid fat content at 20° C. of from 1% to 4%.

* * * * *